US010731132B2

(12) United States Patent
Larsson et al.

(10) Patent No.: US 10,731,132 B2
(45) Date of Patent: Aug. 4, 2020

(54) METHODS AND APPARATUSES FOR UMBILICAL CORD BLOOD COLLECTION AND ISOLATION OF CELLS

(71) Applicant: Amniotics AB, Lund (SE)

(72) Inventors: Marcus Kare Torleif Larsson, Bjarred (SE); Andreas Nils Walter Herbst, Bjarred (SE); Niels-bjarne Roland Woods, Furulund (SE)

(73) Assignee: Amniotics AB, Lund (SE)

( * ) Notice: Subject to any disclaimer, the term of this patent is extended or adjusted under 35 U.S.C. 154(b) by 0 days.

(21) Appl. No.: 14/776,655

(22) PCT Filed: Mar. 14, 2014

(86) PCT No.: PCT/IB2014/001200
§ 371 (c)(1),
(2) Date: Sep. 14, 2015

(87) PCT Pub. No.: WO2014/140921
PCT Pub. Date: Sep. 18, 2014

(65) Prior Publication Data
US 2016/0068815 A1 Mar. 10, 2016

Related U.S. Application Data

(60) Provisional application No. 61/801,280, filed on Mar. 15, 2013.

(51) Int. Cl.
| *C12N 5/0775* | (2010.01) |
| *C12N 5/00* | (2006.01) |
| *C12N 5/071* | (2010.01) |
| *C12N 5/0789* | (2010.01) |

(52) U.S. Cl.
CPC ......... *C12N 5/0665* (2013.01); *C12N 5/0087* (2013.01); *C12N 5/069* (2013.01); *C12N 5/0647* (2013.01); *C12N 5/0692* (2013.01); *C12N 2500/02* (2013.01); *C12N 2506/11* (2013.01); *C12N 2523/00* (2013.01); *C12N 2533/54* (2013.01)

(58) Field of Classification Search
None
See application file for complete search history.

(56) References Cited

U.S. PATENT DOCUMENTS

| 4,308,875 A | 1/1982 | Young |
| 4,567,882 A | 2/1986 | Heller |
| 4,787,894 A | 11/1988 | Turnbull |
| 5,048,530 A | 9/1991 | Hurwitz |
| 5,100,387 A | 3/1992 | Ng |
| 5,395,379 A | 3/1995 | Deutchman et al. |
| 5,494,044 A | 2/1996 | Sundberg |
| 5,951,497 A | 9/1999 | Wallace et al. |
| 6,378,523 B1 | 4/2002 | Christopher |
| 6,461,628 B1 | 10/2002 | Blanchard et al. |
| 6,479,064 B1 | 11/2002 | Atala |
| 6,506,574 B1 | 1/2003 | Rambhatla et al. |
| 6,733,433 B1* | 5/2004 | Fell ..................... A61M 1/3693 435/2 |
| 7,255,879 B2 | 8/2007 | Hariri |
| 7,311,905 B2 | 12/2007 | Hariri |
| 7,596,385 B2 | 9/2009 | Aghvami et al. |
| 7,638,141 B2 | 12/2009 | Hariri |
| 7,682,803 B2 | 3/2010 | Paludan et al. |
| 7,802,574 B2 | 9/2010 | Schultz |
| 7,914,779 B2 | 3/2011 | Hariri |
| 10,143,448 B2 | 12/2018 | Brunner |
| 2005/0042595 A1 | 2/2005 | Haas |
| 2005/0054093 A1 | 3/2005 | Haas |
| 2005/0059152 A1 | 3/2005 | Tanavde et al. |
| 2005/0124003 A1 | 6/2005 | Atala et al. |
| 2005/0148074 A1 | 7/2005 | Davies et al. |
| 2007/0134210 A1 | 6/2007 | Heidaran |
| 2007/0243172 A1 | 10/2007 | Ra et al. |
| 2007/0298497 A1* | 12/2007 | Antwiler .............. C12N 5/0663 435/401 |
| 2009/0191159 A1* | 7/2009 | Sakurada ............. C12N 5/0696 424/93.7 |
| 2010/0124569 A1 | 5/2010 | Abbot et al. |
| 2010/0136679 A1* | 6/2010 | Min ..................... B01L 3/5021 435/325 |
| 2010/0323446 A1 | 12/2010 | Barnett et al. |
| 2012/0190731 A1 | 7/2012 | Messina |
| 2013/0157353 A1* | 6/2013 | Dijkhuizen Borgart ..................... C12M 23/14 435/297.2 |
| 2016/0030489 A1 | 2/2016 | Larsson et al. |

FOREIGN PATENT DOCUMENTS

| AU | 2014201181 A1 | 3/2014 |
| CN | 1407088 A | 4/2003 |

(Continued)

OTHER PUBLICATIONS

Phuc et al., "Isolation of three important types of stem cells from the same samples of banked umbilical cord blood", Cell Tissue Bank, published online Jun. 8, 2011, vol. 13, pp. 341-351.*
Maurice et al., "Isolation of progenitor cells from cord blood using adhesion matrices", Cytotechnology, 2007, vol. 54, pp. 121-133.*
Okabe et al., "Definitive proof for direct reprogramming of hematopoietic cells to pluripotency", Blood, 2009, vol. 114, No. 9, pp. 1764-1767.*
De Wynter et al., "Comparison of Purity and Enrichment of CD34+ Cells from Bone marrow, Umbilical Cord and Peripheral Blood (primed for Apheresis) Using Five Separation Systems", Stem Cells, 1995, vol. 13, pp. 524-532.*

(Continued)

*Primary Examiner* — Laura Schuberg
(74) *Attorney, Agent, or Firm* — Knobbe, Martens, Olson & Bear, LLP (57) ABSTRACT

The invention relates to method for the separation of cord blood endothelial cells from hematopoietic cells in a manner that preserves the hematopoietic cells' repopulating ability and primitivity, without significantly reducing the yield of hematopoietic cells. The said endothelial cells from cord blood have a utility in cell based therapeutics. The system described takes advantage of the endogenous adherence properties of the cells to facilitate the separation and separate storage of the cell types.

20 Claims, 1 Drawing Sheet

(56) References Cited

FOREIGN PATENT DOCUMENTS

| | | |
|---|---|---|
| CN | 202569006 U | 12/2012 |
| DE | 202004012970 U1 | 12/2005 |
| JP | 2005323534 | 11/2005 |
| JP | 2010529851 | 9/2010 |
| JP | 2010265220 | 11/2010 |
| JP | 2011084566 | 4/2011 |
| JP | 2012521780 | 9/2012 |
| JP | 2012255025 | 12/2012 |
| WO | WO 02/35992 A2 | 5/2002 |
| WO | WO 0235992 A2 | 5/2002 |
| WO | WO 03/042405 A2 | 5/2003 |
| WO | WO 03042405 A2 | 5/2003 |
| WO | WO 03/068937 A2 | 8/2003 |
| WO | WO 05078073 | 8/2005 |
| WO | WO 06012404 A2 | 2/2006 |
| WO | WO 10099539 A1 | 9/2010 |
| WO | WO 2012/021845 A2 | 2/2012 |
| WO | WO 12070032 A2 | 5/2012 |
| WO | WO 2016/120310 A1 | 8/2016 |

OTHER PUBLICATIONS

Mareschi et al., "Multipotent Mesenchymal Stromal Stem Cell Expansion by Plating Whole Bone Marrow at a Low Cellular Density: A More Advantageous Method for Clinical Use", Stem Cells International, 2012, vol. 2012, pp. 1-10. (Year: 2012).*

Bieback et al., "Clinical Protocols for the Isolation and Expansion of Mesenchymal Stromal Cells", Transfusion Medicine and Hemotherapy, 2008, vol. 35, pp. 286-294. (Year: 2008).*

Anker et al., "Isolation of Mesenchymal Stem Cells of Fetal or Maternal Origin from Human Placenta," Stem Cells, vol. 22, 2004, p. 1338-1345.

Bongso et al., "Taking Stem Cells to the Clinic: Major Challenges," Journal of Cellular Biochemisty, vol. 105, 2008, p. 1352-1360.

Bottai et al., "Third trimester amniotic fluid cells with the capacity to develop neural phenotypes and with heterogeneity among subpopulations," Restorative Neurology and Neuroscience, vol. 30, 2012, p. 55-68.

Chanda et al., "Retinoic Acid Signaling Is Essential for Embryonic Hematopoietic Stem Cell Development", Cell, vol. 155, No. 1, Sep. 26, 2013, pp. 215-227, XP028729738, ISSN: 0092-8674, DOI: 10.1016/J.CELL.2013.08.055.

Dobreva et al., "On the origin of amniotic stem cells: of mice and men," The International Journal of Developmental Biology, vol. 54, 2010, p. 761-777.

Forraz et al. "The umbilical cord: a rich and ethical stem cell source to advance regenerative Medicine," Cell Proliferation, vol. 44, 2011, p. 60-69.

Friedman et al., "Umbilical Cord Mesenchymal Stem Cells: Adjuvants for Human Cell Transplantation," American Society for Blood and Marrow Transplantation, vol. 13, 2007, p. 1477-1486.

Goichberg et al., "cAMP-induced PKC activation increases functional CXCR4 expression on human CD34+ hematopoietic progenitors", Blood, vol. 107, No. 3, Feb. 1, 2006, pp. 870-879, XP055333120, US ISSN: 0006-4971, DOI: 10.1182/blood-2005-03-0941 p. 876, col. 1, paragraph 1; figures 1-5.

International Search Report and Written Opinion for International Application No. PCT/US17/23090 dated Aug. 15, 2017 in 16 pages.

International Search Report and Written Opinion for International Application No. PCT/IB2016/001628 dated Jan. 24, 2017 in 15 pages.

McGuckin et al., "Culture of embryonic-like stem cells from human umbilical cord blood and onward differentiation to neural cells in vitro," Nature Protocols, vol. 3, 2008, p. 1046-1055.

Mizuno et al., "Generation of skeletal muscle stem/progenitor cells from murine induced pluripotent stem cells," The Journal of the Federation of American Societies for Experimental Biology, vol. 24, 2010, p. 2245-2253.

Murphy et al., "Amnion Epithelial Cell Isolation and Characterization for Clinical Use," Current Protocols in Stem Cell Biology, vol. 13, 2010, p. 1-25.

O'Donoghue et al., "Fetal stem cells," Best Practice & Research Clinical Obstetrics and Gynaecology, vol. 18, No. 6, pp. 853-875, 2004.

Pereira et al., "Reproducible methodology for the isolation of mesenchymal stem cells from human umbilical cord and its potential for cardiomyocyte generation," Journal of Tissue Engineering and Regenerative Medicine, vol. 2, 2008, p. 394-399.

Ronn et al., Reactive Oxygen Species Impair the Function of CD90+ Hematopoietic Progenitors Generated from Human Pluripotent Stem Cells. Sep. 1, 2016, vol. 35, No. 1; pp. 197-206; p. 2, $1^{st}$ column, $2^{nd}$ paragraph to $2^{nd}$ column, $2^{nd}$ paragraph; p. 3, $1^{st}$ column, $1^{st}$ and $2^{nd}$ paragraphs; plage 4, $2^{nd}$ column, $2^{nd}$ paragraph; D0I: 10.1002/stem.2503.

Ronn et al., "Retinoic Acid Regulates Hematopoietic Development from Human Pluripotent Development from Human Pluripotent Stem Cells", Stem Cell Reports, vol. 4, No. 2, Feb. 1, 2015, pp. 269-281, XP055333217, United States ISSN: 2213-6711, D0I: 10.1016/j.stemcr.2015.01.009, p. 271, col. 1, paragraph 2.

Roubelakis, M.G., et al., "In vitro and in vivo properties of distinct populations of amniotic fluid mesenchymal progenitor cells," Journal of Cellular and Molecular Medicine, vol. 15, 2011, p. 1896-1913.

Salehinejad et al., "Comparison of different methods for the isolation of mesenchymal stem cells from human umbilical cord Wharton's jelly," In Vitro Cell.Dev.Biol.—Animal (2012) 48:75-83.

Savickiene et al., "Human Amniotic Fluid Mesenchymal Stem Cells from Second- and Third-Trimester Amniocentesis: Differentiation Potential, Molecular Signature, and Proteome Analysis," Stem Cells International, 2015, in 15 pages.

Saxena et al., "Cyclic AMP Signaling through Epac Axis Modulates Human Hemogenic Endothelium and Enhances Hematopoietic Cell Generation", Stem Cell Reports, vol. 6, No. 5, May 1, 2016, pp. 692-703, XP055333169, United States ISSN: 2213-6711, D0I: 10.1016/j.stemcr.2016.03.006 p. 695, col. 1, paragraph 2; figure 1.

Schiavo, A.A., et al., "Endothelial properties of third-trimester amniotic fluid stem cells cultured in hypoxia," *Stem Cell Research & Therapy*, (2015) 6:209, p. 1-15.

Seshareddy et al. "Method to Isolate Mesenchymal-Like Cells from Wharton's Jelly of Umbilical Cord," Methods in Cell Biology, vol. 86, 2008, p. 101-119.

Vadasz et al., "Second and third trimester amniotic fluid mesenchymal stem cells can repopulate a de-cellularized lung scaffold and express lung markers," Journal of Pediatric Surgery, 2014, in 10 pages.

Weiss et al., "Stem Cells in the Umbilical Cord," Stem Cell Review, vol. 2, 2006, p. 155-162.

You, Q., et al., "Isolation of human mesenchymal stem cells from third-trimester amniotic fluid," International Journal of Gynecology and Obstetrics, vol. 103, 2008, p. 149-152.

Zhou et al., "Generation of human induced pluripotent stem cells from urine samples," Nature Protocols, vol. 7, 2012, p. 2080-2089.

Athanasia D. Panopoulos et al: "Rapid and Highly Efficient Generation of Induced Pluripotent Stem Cells from Human Umbilical Vein Endothelial Cells", PLOS ONE, vol. 6, No. 5, May 16, 2011 (May 16, 2011), p. e19743, XP055035699, DOI: 10.1371/journal.pone.0019743 055035699 X.

Bar-Nur et al. Cell Stem Cell vol. 9, No. 1, 2011, pp. 17-23.

Cao et al.: 'Stem cell repair of central nervous system injury' J Neuroscience Res vol. 68, 2002, pp. 501-510.

Carette et al. Blood vol. 115, No. 20, 2010, pp. 4039-4042.

Eggermann J et al: "Endothelial progenitor cell culture and differentiation in vitro: a methodological comparison using human umbilical cord blood", Cardiovascular Research, Oxford University Press, GB, vol. 58, No. 2, May 1, 2003 (May 1, 2003), pp. 478-486, XP002351441, ISSN: 0008-6363, DOI: 10.1016/S0008-6363(03)00252-9 002351441 1.

Ghosh et al. PLOS ONE vol. 5, No. 2, 2010, p. E8975.

'Guide to Techniques in Mouse Development', 1993, Academic Press.

Hanna et al. Nature vol. 462, No. 7273, 2009, pp. 595-601.

(56) References Cited

OTHER PUBLICATIONS

Ikehata et al. Environ Mol Mutagen vol. 41, No. 4, 2003, pp. 280-292.
Ikehata et al. Mutat Res vol. 556, No. 1-2, 2004, pp. 11-24.
Ingram D A et al: "Identification of a novel hierarchy of endothelial progenitor cells using human peripheral and umbilical cord blood", Blood, American Society of Hematology, US, vol. 104, No. 9, Nov. 1, 2004 (Nov. 1, 2004), pp. 2752-2760, XP002351443, ISSN: 0006-4971, DOI: 10.1182/BLOOD-2004-Apr. 1396 002351443 X.
Kim et al. Nature vol. 467, No. 7313, 2010, pp. 285-290.
Kumano et al. Blood vol. 119, No. 26, 2012, pp. 6234-6242.
L. M. Reid: 'Stem cell biology' Curr. Opinion Cell Biol. vol. 2, 1990, p. 121.
M. V. Wiles: 'Embryonic Stem Cell Differentiation in vitro' Meth. Enzymol. vol. 225, 1993, p. 900.
Marchetto et al. Plos One vol. 4, No. 9, 2009, p. E7076.
Masip et al. Mol Hum Reprod vol. 16, No. 11, 2010, pp. 856-868.
Melissa Ann Brown et al: "Umbilical Cord Blood Derived Endothelial Progenitor Cells: Isolation, Characterization, and Adhesion Potential in Vitro and in Vivo", Jan. 1, 2009 (Jan. 1, 2009), XP055140385, Retrieved from the Internet: URL:http://hdl.handle.net/10161/1355 055140385 X.
Osanai; Lee Med Mol Morphol vol. 44, No. 4, 2011, pp. 200-206.
P. D.Rathjen et al.: 'Properties and uses of Embryonic Stem Cells Prospects for Application to Human Biology and Gene Therapy' REPROD. FERTIL. DEV. vol. 10, 1998, p. 31.
Park et al. Cell vol. 134, No. 5, 2008, pp. 877-886.
Polo et al. Nat Biotechnol vol. 28, No. 8, 2010, pp. 848-855.
Takahashi; Yamanaka Cell vol. 126, No. 4, 2006, pp. 663-676.
Ye et al. Blood vol. 114, No. 27, 2009, pp. 5473-5480.
Yu et al. Science vol. 318, No. 5858, 2007, pp. 1917-1920.
Lindencrona et al. Int J Cancer 2004.
Lee et al., Nature protocols 5:88-701 (2010) vol. 5, No. 4, pp. 688-701.
Panopoulos et al: "Rapid and Highly Efficient Generation of Induced Pluripotent Stem Cells from Human Umbilical Vein Endothelial Cells", PLOS ONE, vol. 6, No. 5, May 16, 2011 (May 16, 2011), p. e19743, XP055035699, DOI: 10.1371/journal.pone.0019743 055035699 X.
Teratocarcinomas and embryonic stem cells: A practical approach', 1987, IRL Press Ltd.
Vizcardo et al. Cell Stem Cell 2013.
Wisniewski et al. (Further phenotypic characterization of the primitive lineage-CD34+CD38-CD9O+CD45Ra-hematopoietic stem cell/progenitor cell sub-population isolated from cord blood, mobilized peripheral blood and patients with chronic myelogenous leukemia. Blood Cancer Journal. 2011).
International Preliminary Report on Patentability for PCT/IB2016/001628 dated Apr. 23, 2019 in 7 pages.
International Preliminary Report on Patentability for PCT/IB2016/O01628 dated Mar. 17, 2017 in 6 pages.

* cited by examiner

METHODS AND APPARATUSES FOR UMBILICAL CORD BLOOD COLLECTION AND ISOLATION OF CELLS

RELATED APPLICATION

This application is a U.S. National Stage Application of International Application No. PCT/IB2014/001200, filed Mar. 14, 2014, which claims priority to U.S. Provisional Patent Application Ser. No. 61/801,280, filed on Mar. 15, 2013. The contents of the above-identified applications are incorporated by reference herein in their entireties for all purposes.

TECHNICAL FIELD

In one embodiment, the invention described herein relates to obtaining biological material, including human umbilical cord blood, including at birth, and in some aspects relates to safe, efficient, high-yield collection of sterile umbilical cord blood and devices and methods for the same. In another embodiment, the invention relates to cells and cultures of cells derived from umbilical cord blood, and methods for extracting, isolating, maintaining, expanding, reprogramming, differentiating, and storing the cells. It also relates to uses of the cells in therapeutics, treatment, disease prevention, drug discovery, personalized medicine, regenerative medicine, tissue generation, and universal donor banks, and related methods and compositions.

BACKGROUND

Methods for isolating cells, cell reprogramming, generating pluripotent and multipotent cells, and tissue, organ, and stem cell therapies, are needed for a variety of therapeutic applications, including personalized and regenerative medicine. A variety of human stem cells and other cell types are known, including embryonic stem cells, isolated during early embryonic development, and somatic stem cells such as mesenchymal or adult stem cells. Some non-stem cells can be reprogrammed into more primitive stages.

Human umbilical cord blood from newborn infants has been used as a source of hematopoietic stem cells for transplantation to patients with hematological disorders and malignancies for decades, due to the high proportion of blood stem cells present in the material. As such, there are currently hundreds of thousands of cord blood samples stored around the world in publicly and privately financed storage banks, ready to be used upon request.

In addition to hematopoietic stem cells, other cell types (e.g., non-hematopoietic cells), are also present in umbilical cord blood samples. Some of these cells have been isolated and characterized for possible therapeutic applications. For example, isolated and expanded endothelial cells from umbilical cord blood have been used in cell therapy for cardiac tissue repair. Due to the low frequency of the endothelial cell population (less than 2% in umbilical cord blood), and the limited availability of technologies for endothelial cell based therapeutics, isolation of endothelial cells from umbilical cord blood is not commonly used in the clinical setting.

Available approaches and apparatuses for collecting, extracting, and isolating biological components, including cellular material, umbilical cord blood, and cells found therein, have not been entirely satisfactory, for example, in their safety, avoidance of contamination (e.g., air contamination) of collected material, cell yield, efficiency, and/or ability to avoid destruction of components.

Methods for isolating stem cells and/or generating multipotent and/or pluripotent stem cells from more differentiated cells are needed, for example, for cell based therapeutic applications, including regenerative medicine, and personalized medicine (individually optimized therapy). Cell sources and isolation methods are needed in this regard. There also is a need for source material cells that can be harvested conveniently from a large number of donors, for example, for isolation of cells in high numbers and that are capable of being manipulated. Provided are embodiments that address such needs.

For example, there is a need for methods and apparatuses for safe, high-yield collection of sterile umbilical cord blood, with minimal destruction of umbilical cord blood components, for retrieval, propagation, and differentiation of components, including cells, and for safe and reliable methods for extracting and isolating cellular material with the potential for reprogramming thus generating pluripotent and multipotent cells, and, without compromising existing sources of therapeutically relevant cells.

There is a need for methods for isolating cells, including non-blood cells, from umbilical cord blood samples, for example, without disrupting the function of other cell types in cord blood, such as hematopoietic stem cells. Among the embodiments provided herein are methods, apparatuses, and compositions that address these needs.

Likewise, there is a need for cells that are abundant and capable of manipulation, reprogramming, and differentiation, for use in regenerative medicine, treatment and disease prevention, personalized medicine, tissue generation. Universal donor banks are also needed. Among the provided embodiments are methods, apparatuses, cells, and compositions that address these needs.

SUMMARY

Provided herein is a method for isolating endothelial cells, comprising: (a) plating an umbilical cord blood sample on a surface; and (b) allowing adhesion of cells in said cord blood sample to said surface, wherein said adherent cells comprise said endothelial cells.

In another embodiment, a method for isolating endothelial cells and hematogenic progenitor cells is provided. The method comprises: (a) plating an umbilical cord blood sample on a surface; (b) allowing adhesion of cells in said cord blood sample to said surface; (c) separating non-adherent cells from said adherent cells, wherein said adherent cells comprise said endothelial cells, and said non-adherent cells comprise said hematogenic progenitor cells. In one aspect, step (c) does not cause significant detachment of said adherent cells from the surface. In another aspect, at least about 10%, about 20%, about 30%, about 40%, about 50%, about 60%, about 70%, about 80%, about 85%, about 90%, about 95%, or about 99% of said adherent cells remain attached to the surface following step (c).

In any of the embodiments described herein or any combination thereof, the umbilical cord blood sample can be from a human. In any of the embodiments described herein or any combination thereof, the umbilical cord blood sample can be freshly harvested or frozen. In any of the embodiments described herein or any combination thereof, the umbilical cord blood sample can be processed for mononuclear cell enrichment. In other embodiments, the umbilical cord blood sample is not processed for mononuclear cell enrichment. In any of the embodiments described herein or any combination thereof, the umbilical cord blood sample can be processed for hematopoietic progenitor and/or hematopoietic stem cell enrichment. In other aspects, the umbilical cord blood sample is not processed for hematopoietic progenitor and/or hematopoietic stem cell enrichment.

In any of the embodiments described herein or any combination thereof, the umbilical cord blood sample is plated at a temperature between about 0° C. and about 37° C. In one embodiment, the surface is coated with collagen I, or gelatin, or a similar extracellular matrix component, or any combination thereof. In some aspects, cells in said cord blood sample are allowed to adhere to said surface for about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes or longer.

In any of the embodiments described herein or any combination thereof, the surface onto which a umbilical cord blood sample is plated can be a surface comprised in any suitable plate (e.g., a tissue culture plate), dish, vessel, chamber, bag (e.g., a blood collection bag), container or the like. In preferred embodiments, the surface is horizontally positioned or essentially horizontally positioned.

In any of the embodiments described herein or any combination thereof, the method further comprises providing suitable conditions for maintaining hematopoietic cell viability, primitivity and/or repopulating ability. In other embodiments, the method further comprises providing suitable conditions for maintaining endothelial cell viability and/or primitivity.

Also disclosed herein is a method of generating a stem cell or progenitor cell, comprising reprogramming the endothelial cell isolated by a method disclosed in any of the foregoing embodiments, to a stem cell or progenitor cell. Provided herein is a method of obtaining a stem cell or progenitor cell, comprising expanding the hematogenic progenitor cell isolated by a method disclosed in any of the foregoing embodiments, and optionally: (1) isolating a more primitive cell from said expanded hematogenic progenitor cell population, or (2) reprogramming said hematogenic progenitor cell to a stem cell or progenitor cell.

Provided herein is a method of generating a somatic cell, comprising: (a) reprogramming the endothelial cell isolated by a method disclosed in any of the foregoing embodiments to a stem cell or progenitor cell, and differentiating said stem cell or progenitor cell to a somatic cell; or (b) reprogramming the endothelial cell isolated by a method disclosed in any of the foregoing embodiments to a somatic cell directly.

Also provided herein is a dual vessel device for isolating cells from umbilical cord blood, comprising two vessels and a tubing with stopcock flow regulation for the transfer of cells in suspension between the vessels. In one embodiment, the dual vessel device further comprises a media chamber attached in a closed system with stopcock flow regulation to facilitate cell washing and cell transfer to the vessels. In one aspect, the dual vessel device further comprises one or more auxiliary chambers to facilitate the administration of cryoprotectant to the vessels. In one embodiment, the dual vessel device is prefilled with a hypoxic, normoxic, or hyperoxic gas.

DETAILED DESCRIPTION

A. Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. In another example, a description of a range in weeks also includes disclosure of the days between the week endpoints. This applies regardless of the breadth of the range.

As used herein, the term "safe" can be understood to refer to any method or apparatus which poses no significant risk of maternal and/or fetal harm.

As used herein, "isolated," when used to describe a cell or cells, refers to a cell or cells that have been separated from their natural environment, including by separation from the subject from which the cell is derived, e.g., a patient, and/or by separation from one or more other components of the natural environment, such as debris, tissue, tissue aggregates, and other cells.

As used herein, "fetal" is used to describe the property of a cell or other material derived from a developing mammal, such as a human, after the embryonic stage and before birth.

As used herein, "infant" is used to describe the property of a cell or other material derived from a newborn or young mammal, from birth to one year of age, including premature infants and newborns.

As used herein, "pluripotent" refers to the ability of a cell to differentiate into cell types of any of the three germ layers, endoderm, mesoderm, and ectoderm. "Multipotent" refers to the ability of a cell to differentiate into cells of a number of multiple, but a limited number of lineages.

In the following description of certain embodiments provided here, reference is made to the accompanying drawings which form a part hereof, and in which it is shown by way of illustration specific embodiments in which the invention can be practiced. It is to be understood that other embodiments can be used and structural changes can be made without departing from the scope of the invention.

B. Umbilical Cord Blood and Umbilical Cord Blood Cell Separation

Among the provided embodiments are apparatuses, devices, and methods for collection, isolation, and use of biological materials, including cell and cellular sources, such as those obtained from umbilical cord blood, as well as cells and other materials obtained by such methods, and uses thereof, including therapeutic and analytic uses, for example, in regenerative medicine, including personalized and universal donor applications.

A variety of human stem cells are being used therapeutically or evaluated for use in clinical trials, including somatic cells, such as mesenchymal stem cells, and hematopoietic stem cells, e.g., for use in neurological and hematological disorders, respectively. Other somatic cells of more differentiated capacities can be reprogrammed into more primitive stages, for example reprogramming of endothelial cells into pluripotent stem cells.

Induced pluripotent stem (iPS) cells have been generated from multiple cell types, including skin and fibroblasts. Masip et al., 2010, Mol Hum Reprod 16(11): 856-868; Takahashi and Yamanaka, 2006, Cell 126(4): 663-676; Yu et al., 2007, Science 318(5858): 1917-1920. Alternative starting materials have been chosen based on: ease of reprogramming, including sufficient proliferation rates, genetic background for disease modeling, ease of harvesting sufficient numbers of viable cells, and genomic integrity. Hanna et al., 2009, Nature 462 (7273): 595-601; Park et al., 2008, Cell 134(5): 877-886; Ye et al., 2009, Blood 114(27): 5473-5480; Carette et al., 2010, Blood 115(20): 4039-4042; Kumano, et al., 2012, Blood 119(26):6234-6242; Ikehata et al., 2003, Environ Mol Mutagen 41(4): 280-292; Ikehata et al., 2004, Mutat Res 556(1-2): 11-24; Osanai and Lee, 2011, Med Mol Morphol 44(4): 200-206.

Available methods for generating iPS cells have been associated with certain problems. For example, adult skin fibroblasts, from which a majority of iPS cells are generated. Nonetheless, due to epigenetic memory, the residual epigenetic state of a cell used as a source for iPS generation can influence the differentiation capacity of derived iPS cells. Specifically, iPS cell lines can maintain an epigenetic memory of tissue origin by continuing to express a key set of donor cell genes. Marchetto et al., 2009, PLoS One 4(9): e7076; Ghosh et al., 2010, PLoS One 5(2): e8975; Bar-Nur et al., 2011, Cell Stem Cell 9(1): 17-23. Epigenetic memory can impact differentiation capacity of many cellular sources, which can make certain differentiated cells (such as neural progenitor cells, certain blood lineage cells, fibroblasts, myogenic cells, pancreatic islet beta cells and other pancreatic cells) less desirable for iPS generation. Kim et al., 2010, Nature 467(7313): 285-290; Polo et al., 2010, Nat Biotechnol 28(8): 848-855; Bar-Nur et al., 2011, Cell Stem Cell 9(1): 17-23; Marchetto et al., 2009, PLoS One 4(9): e7076; Ghosh et al., 2010, PLoS One 5(2): e8975.

Thus, more primitive cells with multipotent differentiation capacities in some contexts are a more appropriate starting material for iPS cell generation, with broad differentiation capacities.

In some contexts, naïve cells that have had minimal contact with the environment, contain undamaged genome(s), and/or have the ability to proliferate and/or expand in an in vitro culture system, are desired for cell reprogramming, e.g., for tissue, organ, and/or stem cell based therapies. Certain cellular material derived from a term or near term fetus or newborn child would fulfill those characteristics. At birth, cellular sources, e.g., umbilical cord blood, contain cells having such characteristics.

Umbilical cord blood is a source typically used for hematopoetic stem cell transplantation. Cord blood hematopoietic stem cells have a naïve state with minimal exposure to the environment (intact genome), high proliferation capacity, and differentiation potential. Within the umbilical cord blood, there exist non-blood cell types at low frequency numbers that are well suited for cell and regenerative medical purposes, for example, the endothelial cell fraction of the umbilical cord blood. The availability of reprogramming technologies, e.g., as described by Takahashi and Yamanaka, 2006, Cell 126(4): 663-676, whereby cells of a particular lineage can be "reprogrammed" into lineages of another type or into an embryonic-like state, increases the value of rare cell fractions present in the umbilical cord blood, which may be used as a source for reprogramming and cell therapeutics.

Available approaches and apparatuses for collecting, extracting, and isolating biological components, including cellular material, umbilical cord blood, and cells found therein, have not been entirely satisfactory, for example, in their safety, avoidance of contamination (e.g., air contamination) of collected material, cell yield, efficiency, and/or ability to avoid destruction of components.

With umbilical cord blood collection, certain negative consequences for the infant can arise if the cord is clamped early. Available methods of culturing hematopoetic stem cells (HSCs) from cord blood have failed to maintain the repopulating ability of the hematopoetic stem cells. Most available separation procedures involve culture incubations which have deleterious effects on the HSC pool. Use of cord blood harvested by available methods in reprogramming applications can decrease or entirely obviate its full hematopoietic potential (a main reason for inclusion into the donor bank system). Methods are needed for obtaining non-blood cells from cord blood samples without disturbing the utility of the hematopoetic stem cell fraction. Particularly because millions of cord blood samples are stored in banks over the world, methods are needed for isolating and expanding these cells without disturbing the function of the hematopoietic stem cell fraction, which is commonly used for therapeutic purposes.

Takahashi and Yamanaka first described reprogramming technologies to "reprogram" or "de-differentiate" somatic cells into a pluripotent/embryonic like state, or to directly "reprogram" somatic cells into another cell lineage type. Takahashi and Yamanaka, 2006, Cell 126(4): 663-676. Thus, the rare endothelial cell fraction present in umbilical cord blood can be used as a starting material for reprogramming and cell therapeutics. The properties of these cells make them amenable to reprogramming In one embodiment, the cell type isolated from umbilical cord blood using the present invention is an endothelial progenitor cell. The cord blood derived endothelial progenitor cells are suitable for reprogramming, and the principle advantages include that they are adherent, fast dividing, primitive (in that they are progenitor cells with corresponding proliferative/differentiation potential and epigenetic profile), and that they are from a neonatal source. Additionally, the cord blood derived endothelial progenitor cells experience reduced exposure to mutagens, and therefore likely have reduced accumulation of genomic mutations in comparison to adult patient sources of cells. In one embodiment, the endothelial cells are harvested in a manner that does not harm the function of, or substantially reduce the numbers of hematopoietic stem cells from the cord blood. Thus, the present invention provides added value to cord blood samples beyond their use in hematopoietic stem cell transplantations.

In one embodiment, the invention described herein provides a system that allows efficient harvest of endothelial cells with minimal loss of therapeutically valuable hematopoietic stem cells from human umbilical cord blood. In one aspect, the present invention provides simultaneous and fast isolation of the adherent endothelial progenitor cells from the umbilical cord blood, which possess reprogramming ability and therefore potentially great therapeutic value. In a preferred embodiment, the ability of umbilical cord blood to provide hematopoietic stem cells is largely maintained or unaffected.

Human umbilical cord blood endothelial progenitor cells can be isolated using Ficoll gradient centrifugation and direct plating of mononuclear cell fractions. The isolated cells are plated either directly onto a gelatin or collagen I coated surface, or are plated following further purification using magnetic beads for progenitor markers such as but not limited to CD34 and CD133. Cells are then cultured for days or weeks using an endothelial cell culture media. At this point, an expanded adherent layer of endothelial cells/progenitors is visible and is taken for extraction. However, this process renders the hematopoietic progenitor and stem cells unsuitable for transplantation, as the in vitro conditions for the endothelial progenitor cell growth do not allow the hematopoietic stem cell to be maintained. Under such conditions, large scale differentiation of primitive progenitor cells occurs. Moreover, with regular media changes, the hematopoietic cell fraction is removed and discarded, as it is no longer capable of reconstituting the hematopoietic system following transplantation.

The present invention increases the therapeutic value of human umbilical cord blood by enabling the separation, storage and use of both hematopoietic cells and endothelial cells. In one embodiment, the present invention does not rely on culturing the cells, or culturing the cells for an extended period of time. In a preferred embodiment, the viability and functionality of the traditional therapeutically valuable hematopoietic stem/progenitor cell fraction are preserved, while at the same time, viable and functional endothelial cells are isolated.

Prior work has shown the ability to isolate endothelial progenitor cells from umbilical cord blood. These progenitors have the potential of large scale expansion and replication whilst maintaining the differentiation potential for the endothelial lineage. This population is defined by its ability to form tubular-like structures of capillary morphology in culture systems. Recently, it has been demonstrated that cord blood derived endothelial cells, including AC133$^+$ cells and CD34$^+$ endothelial cells, can be used to efficiently generate iPS cells. This means that these cells are capable of being efficiently reprogrammed to a pluripotent stem cell state with properties similar to embryonic stem cells. However, previously employed methods either harmed or impaired cell function, or reduced the numbers of hematopoietic stem cells. For example, endothelial cells and hematopoietic progenitor and stem cells express some common markers on their surfaces, such as CD34, CD31, VEGFR, and AC133. Isolating endothelial cells from cord blood by targeting these markers therefore leads to the isolation of a mixture of endothelial cells and hematopoietic progenitor and stem cells. Targeting these common markers also results in a loss of the hematopoietic cells. For example, the yield of hematopoietic cells by selecting for CD45$^+$ cells using magnetic beads is at best 70%. Thus, there is approximately a 30% reduction in hematopoietic cell yield, and it takes hours to process the cells, causing considerable risk to the quality of the isolate cells. Although sorting based methods result in high purities of cell fractions, they have even lower yields of approximately 50%.

Extended culturing of the total umbilical cord cells is another method used for separating endothelial cells from the hematopoietic cell fraction. These cell culture procedures typically take 7-14 days. Endothelial cells are seeded to form colonies and they eventually form adherent layers on the plates, whereas the hematopoietic fraction will remain in suspension or only become weakly adherent. Such lengthy cell culture of hematopoietic stem cells, or even short-term exposure to in vitro incubations, have been shown to seriously alter transcriptional profiles of hematopoietic stem cells (HSCs), and more importantly, to reduce functional repopulating efficiencies of the HSCs. As such, there is need for an alternative method for separating the endothelial cell fraction and the hematopoietic stem cell fraction.

An alternative method of obtaining relatively pure endothelial cells from the umbilical cord is the procedure to isolate human umbilical vein endothelial cells (HUVECs). However, the procedure to isolate HUVECs must be done at the time of the cord blood harvest, prior to the cord being discarded, because the cells are derived from the endothelium of the cord itself and not from the cord blood located within the vessels of the cord. Because the procedure of harvesting HUVECs is complicated by the necessity for cord tissue processing, which includes manual isolation and desiccation of the cord tissue, as well as an enzyme-based cellular disassociation step (for example, by trypsinization), all under clinically approved cell-processing laboratories, this procedure is not possible in most hospitals worldwide. As such, most cord blood samples currently stored in biobanks do not include HUVECs. Moreover, the procedure to harvest HUVECs takes days to weeks before significant numbers of the endothelial cells can be harvested for freezing and storage. However, the procedure of harvesting blood from the human umbilical cord into a sterile vessel is routine in many clinics worldwide. In one embodiment, provided herein is a method to separate cell types present in cord blood. Thus, the present invention addresses the requirements of ease of use, sterility, and preservation of cellular material, without significantly affecting the procedure of cord blood harvesting performed by these clinics.

Typical harvesting of cord blood in labor wards is performed by first clamping and cutting the umbilical cord, followed by extracting the blood usually either through a needle which punctures the cord vein and arteries, with attached closed system catheter into a sterile collection bag, or simply by draining the cord blood from the cord cut site opening into a collection vessel. Gravity or physical manipulation of the cord aids in the extraction of blood from the cord into the collection vessel. The collection vessel usually contains an anti-coagulant (e.g., heparin sulfate, citric acid, or EDTA). If the cord blood sample is to be frozen for storage, it may contain a cryoprotectant such as DMSO. In some aspects, cord blood is processed for progenitor/stem cell enrichment, for example, as outlined above using clinical grade antibody bound magnetic beads.

In one aspect, an embodiment of the present invention is to provide a rapid and clinically applicable system for the separation of endothelial progenitor cells from hematopoietic cells from human umbilical cord blood in order to obtain a clinically valuable endothelial cell type, while preserving the yield and repopulating ability of the hematopoietic stem cells. This embodiment allows for additional use of cord blood samples. In one embodiment, newly harvested cord blood samples are used. In other embodiments, previously processed and stored frozen samples are used. In one aspect, samples of total or mononuclear cell fractions of cord blood are used. In another aspect, samples processed for progenitor enrichment are used. In one aspect, the present invention takes advantage of the differences in cell surface adhesive properties between the hematopoietic cell fraction and the endothelial cell fraction, thereby enabling the separation of the two cell types. In one embodiment, the cord blood sample is plated on a coated plate. The separation procedure is performed following a short incubation of the cells on the plate, and is capable of being performed at the bedside. The present invention overcomes limitations of current technologies that result in reduced viability, yield and quality of the hematopoietic cells.

The proper use of the different and specific binding characteristics of cord blood hematopoietic cells and endothelial cells, with regard to ligand affinity and time dependent binding, may be employed for separating these two cell types. For example endothelial cells express V-CAM, VE-cadherin, E-selectin, and VLA-1 (integrin α1β1), which are cell binding factors that promote signaling between these cells and their niche cells. Accordingly, these and other endothelial cell markers can be specifically exploited for the separation of these cells from the hematopoietic cells, which do not express these markers or only weakly adhere to the endothelial receptors. While the hematopoietic fraction is considered a suspension cell type, there are weak adhesion ligands expressed on these cells, such as CXCR4. CXCR4 binds the chemokine SDF-1 which is bound to the extracellular matrix component fibronectin. Moreover, integrins such as VLA-1 and VLA-4 are also expressed on hematopoietic cells, and VLA-1 and VLA-4 bind to collagen and VCAM 1, respectively. There are additional weak adherence factors in non-tissue damaged hematopoietic cell types. The present invention provides a cell collection device, vessel, or culture chamber coated with the ligands or epitopes of the above mentioned endothelial adherence factors, for hematopoietic cell and endothelial cell separation.

In the present invention, recently thawed or freshly obtained cord blood or the progenitor enriched cell fractions can be separated following exposure to specific adherence factors in a sterile, pre-coated vessel. The specific coating can be achieved by a specific polymer/protein mixture. In addition, coatings that resemble the extracellular matrix or its components (e.g. gelatin, or collagen I) may be employed. The coating is covered by a minimal supportive media (clinical use grade) for maintaining cellular viability during the procedure. In some embodiments, mononuclear cell enriched cord blood sample, or progenitor or stem cell enriched cord blood sample, can be plated at approximate 10 million cells per 100 $cm^2$ in a plate or dish. In some embodiments, cord blood sample not processed for cellular subtype enrichment, or cord blood sample not processed for erythrocyte reduction, is plated at approximate 100 million cells per 100 $cm^2$ in a plate or dish. In one embodiment, the total volume of media is at least 10 mL per 100 $cm^2$. In one aspect, upon plating, the vessel containing the cells and the media is placed onto a solid surface to allow for the cells to attach to the surface of the vessel. In some aspects, the cells are incubated at room temperature, in a 4 degrees Celsius refrigerator, or in a 37 degree Celsius incubator, depending on the binding affinity and property of the specific coating used in the separation vessel. In some embodiments, within 5 minutes the majority of endothelial cells are loosely attached to the coated surface. In other embodiments, by 15 minutes the cells are sufficiently attached, so that the surface can be washed to remove the non-adherent hematopoietic cell fractions, for example, with 3 rounds of washing with media. The hematopoietic cells in suspension from the wash can be processed for freezing using a cryoprotectant. Simultaneously, the remaining adherent endothelial cell fraction on the coated surface is resubmerged in media with cryoprotectant for freezing and storage. In another embodiment, the remaining adherent endothelial cell fraction on the coated surface is processed by mild trypsinization to disassociate the cells from the coating, so that the cells can be further cultured in a suitable endothelial cell medium for extended culture and expansion of the endothelial cells.

In the case where cord blood is harvested in a sterile manner using a needle and catheter system to collect the blood directly, the invention also provides a cell-separation procedure that can be performed at the bedside of patients. In one embodiment, such beside separation procedure is performed with a catheter draining into the sterile pre-coated separation vessel directly, followed by incubation of the collected cord blood and washing of the hematopoietic fraction into a new non-coated vessel. In one aspect, the present invention provides a dual vessel linked closed collection system for direct freezing and storage. In one preferred embodiment, the present invention obliterates the need for culturing or processing of cells in a laboratory setting.

Also provided are methods for expanding, reprogramming, and differentiating the isolated cells and cellular fractions, and methods for use of the same, e.g., for cellular and tissue generation, regenerative and personal medicine, disease treatment, and other processes.

Also provided are methods for optimizing use of cord-blood samples. In some aspects, such methods allow the use of a medically relevant cell fraction constituent otherwise not available for use. In one aspect, such methods and cell fractions are useful for enhancing the value of already established cord-blood donor banks, by permitting a dual use: (1) use of the cells for haematopoietic reconstitution in a patient and (2) use of other cells present in the cord blood for regenerative medicinal purposes.

C. Device for Cord Blood Collection and Cell Separation

The invention also relates to a device for the efficient harvesting and separation of the cellular components of the cord blood material employing the principal workings of the method outlined above. One such embodiment comprises a sterile dual-vessel closed collection system, where one of the vessels is pre-coated for endothelial cell attachment. When the cord blood sample is ready for processing, either having been freshly harvested in a separate collection vessel, or having been processed for progenitor cell enrichment and placed in separate temporary storage vessel, or having been recently thawed in a storage vessel, the umbilical cord blood or enriched cells are transferred to the vessel with the endothelial cell adherence coating (vessel 1). The transfer of the cord blood material to vessel 1 can be performed by directly connecting vessel 1 to the collection/storage vessel containing blood or cells via a needle and catheter tubing from the vessel and into the coated vessel 1. Following transfer to vessel 1, cells are incubated for the appropriate time and at the appropriate temperature depending on the adherence factors used in the coating on a flat horizontal surface. Following the cell-adherence incubation step, the non-adherent fraction of cells in suspension is transferred to the hematopoietic cell collection vessel (vessel 2) which is connected to the coated bag via a sterile tubing. Wash medium stored in one or more separate sealed storage chambers attached to the vessel 1 can then be transferred into vessel 1, in three separate wash steps (25-100 mL each). In one embodiment, a stopcock valve or equivalent structure is located on the tubing between the medium chamber and vessel 1. The wash media with suspension of hematopoietic cells is then transferred to the hematopoietic collection vessel (vessel 2) via a closed tubing. Again, a stopcock valve system or equivalent may be employed in this structure. After the transfer, the adherent fraction in vessel 1 is re-submerged in media and an auxiliary chamber with cryoprotectant is opened to release an appropriate volume of cryoprotectant, and the adherent cells are directly frozen. Vessel 2 also has an auxiliary cryoprotectant buffer chamber, thus hematopoietic suspension can be frozen directly.

The pre-coated vessel 1 with attached needle and catheter tubing can be used to harvest cord blood directly from the umbilical cord. This allows the separation to proceed directly following the harvest. The separation of hematopoietic cells and endothelial cells occurs as detailed above. This system allows for a quick and simple processing of cord blood cell fractions in a closed system that can be performed with sterility at the bedside.

D. Isolation, Culture, Sub-Culture, Reprogramming and Differentiation of Cells Derived from Cord Blood Also provided are methods for isolation of cells from cord blood, e.g., collected using the methods and apparatuses provided herein.

Cells can be counted to determine yield. In one embodiment, the procedure yields at least at or about 10%, 20%, 30%, 40%, 50%, 60%, 70%, 80%, 90% viable cells. In preferred embodiments, the procedure yields at least at or about 50% viable cells.

In some embodiments, the isolated cells are cultured, for example, to expand the cells. In one example, the cells are transferred to a culture receptacle, e.g., flask, containing a growth medium appropriate for the desired cell-type. In one embodiment, a fibroblast growth medium is used. In one embodiment, a mesenchymal stem cell growth medium is used. In one embodiment, an endothelial cell growth medium is used. In one embodiment, a small-airway epithelial growth medium is used. Without being bound by any theory, other cell culture medium may be used in certain embodiments. In one aspect, the isolated cells are cultured in the medium for at least or about one week, two weeks, three weeks, four weeks, or five weeks. In certain aspects, the isolated cells are cultured in the medium for at least or about 11, 12, 13, 14, 15, 16, 17, 18, 19, 20, 21, 22, 23, 24, 25, 26, 27, 28, 29 or 30 days. Flow cytometry, microscopy, and other known procedures may be used to assess the behavior and phenotype of the cultured cells.

In one embodiment, the cells are propagated, e.g., in sub-cultures. In one example, the cells are propagated for at least at or about 10, 20, 30, 40, 50, 60, or 70 days, or for 30 population-doublings, or until the cells have expanded at least 10,000-, 100,000-, 200,000-, 300,000-, 400,000-, 500,000-, or 1 million-, 2 million-, or 3 million-fold, or until the cells have reached senescence or until just before the cells reach senescence.

In one embodiment, high expression of Oct-4 is maintained by secondary culture in hypoxic conditions, corresponding to the low oxygen tension in-utero.

Also provided are methods for reprogramming and differentiating the cells, for example, to generate desired types of cells or tissues, such as for regenerative therapeutic applications. In certain embodiments, the cells are reprogrammed to a less-differentiated stage, such as to a pluripotent or multipotent stage. Reprogramming methods, such as induction of pluripotent stem cells (iPSC) are well-known and may be used to revert the differentiation of the cells to generate pluripotent or multipotent cells. Exemplary methods are described in Takahashi and Yamanaka, 2006, Cell 126(4): 663-676, and in Yu et al., 2007, Science 318(5858): 1917-1920.

In some embodiments, the cells, e.g., pluripotent or multipotent cells, are differentiated into desired cell- or tissue-types. In one aspect, the cells are cultured under conditions for generation of a desired cell type or tissue type, for example, endodermal, ectodermal, or mesodermal-derived tissues, such as liver cells or tissue, endocrine tissue, lung cells or tissue, blood cells, bone marrow cells, neuronal cells, astroglial cells, heart cells or tissue, e.g., cardiomyocytes, ocular cells or tissue, nerve cells or tissue, brain cells or tissue, muscle cells or tissue, skin cells or tissue, pancreatic cells or tissue, e.g., beta cells, adipogenic cells, chondrogenic cells, osteogenic cells, and neural cells. In certain embodiments, the cells are differentiated into neurons, hepatocytes, pancreatic islet cells, kidney cells, and hematopoietic cells, among other cell types. In some embodiments, the cells are differentiated into cell types representing all three germ layers. In some embodiments, the cells maintain an efficient differentiation capacity across germ layers following reprogramming In one aspect, the cells possess a higher blood generation capacity compared to human embryonic stem cells or cell lines. One such human embryonic stem cell line is H9. In another aspect, the cells possess near 100% neuronal cell differentiation capacity. In some embodiments, the cells are differentiated to osteoblasts or adipocytes.

Differentiation methods are well-known. Any of a number of known methods may be used in connection with this embodiment, for example, the methods described in U.S. Pat. No. 7,596,385, U.S. Patent Publication Numbers US 2005/0054093 and US 2005/0042595, all to Haas, and in U.S. Patent Publication Number US 2005/0124003 and International Patent Application No. WO 03/042405, to Atala et al., and methods described in "Teratocarcinomas and embryonic stem cells: A practical approach," E. J. Robertson, ed., IRL Press Ltd. 1987; "Guide to Techniques in Mouse Development," P. M. Wasserman et al. eds., Academic Press 1993; "Embryonic Stem Cell Differentiation in vitro, M. V. Wiles, Meth. Enzymol. 225: 900, 1993; "Properties and uses of Embryonic Stem Cells Prospects for Application to Human Biology and Gene Therapy," P. D. Rathjen et al., Reprod. Fertil. Dev. 10: 31, 1998; and in "Stem cell biology," L. M. Reid, Curr. Opinion Cell Biol. 2: 121, 1990.

Differentiation-inducing agents, maturation agents, and maturation factors also are well-known for differentiation to particular cell types, such as agents described in U.S. Pat. No. 6,506,574, to Rambhatla et al., e.g., N-butyrate, for differentiation into liver cells, and other maturation agents, maturation factors, growth factors, peptide hormones, cytokines, ligand receptor complexes, corticosteroids, retinoic acid, and organic solvents, such as DMSO, glucocorticoid with cAMP-elevating agents, methyl-isobutylxanthine, and indomethacin. Choice of differentiation agent(s) will depend on desired cell or tissue type.

The cells, compositions, and tissues provided herein, such as differentiated cells, are useful for the treatment of diseases, such as, but not limited to, infertility, cirrhosis of the liver, pancreatitis, diabetes, Parkinson's disease, spinal cord injury, stroke, burns, heart disease, osteoarthritis, rheumatoid arthritis, cancers, such as leukemia, e.g., Acute Lymphoblastic Leukemia, Acute Myelogenous Leukemia, Acute Biphenotypic Leukemia, and Acute Undifferentiated Leukemia; Chronic Myelogenous Leukemia, Chronic Lymphocytic Leukemia, Juvenile Chronic Myelogenous Leukemia, Juvenile Myelomonocytic Leukemia, lymphoma, e.g., Non-Hodgkin's Lymphoma, Hodgkin's Disease, Multiple Myeloma, Plasma Cell Leukemia, Breast Cancer, Ewing Sarcoma, Neuroblastoma, Renal Cell Carcinoma, genetic blood disorders, brain disorders such as Alzheimer's disease, Refractory Anemia, Refractory Anemia with Ringed Sideroblasts, Refractory Anemia with Excess Blasts, Refractory Anemia with Excess Blasts in Transformation, Aplastic Anemia, Fanconi Anemia, Paroxysmal Nocturnal Hemoglobinuria, Pure Red Cell Aplasia, Acute Myelofibrosis, Agnogenic Myeloid Metaplasia, myelofibrosis, Polycythemia Vera, Essential Thrombocythemia, Chediak-Higashi Syndrome, Chronic Granulomatous Disease, Neutrophil Actin Deficiency, Reticular Dysgenesis, Mucopolysaccharidoses, Hurler's Syndrome, Scheie Syndrome, Hunter's Syndrome, Sanfilippo Syndrome, Morquio Syndrome, Maroteaux-Lamy Syndrome, Sly Syndrome, Beta-Glucuronidase Deficiency, Adrenoleukodystrophy, Mucolipidosis II, Krabbe Disease, Gaucher's Disease, Niemann-Pick Disease, Wolman Disease, Metachromatic Leukodystrophy, Familial Erythrophagocytic Lymphohistiocytosis, Histiocytosis-X, Hemophagocytosis, Inherited Erythrocyte Abnormalities, Beta Thalassemia Major, Sickle Cell Disease, Inherited Immune System Disorders, Ataxia-Telangiectasia, Kostmann Syndrome, Leukocyte Adhesion Deficiency, DiGeorge Syndrome, Bare Lymphocyte Syndrome, Omenn's Syndrome, Severe Combined Immunodeficiency, Common Variable Immunodeficiency, Wiskott-Aldrich Syndrome, X-Linked Lymphoproliferative Disorder, Other Inherited Disorders, Lesch-Nyhan Syndrome, Cartilage-Hair Hypoplasia, Glanzmann Thrombasthenia, Osteopetrosis, Inherited Platelet Abnormalities, Amegakaryocytosis, Congenital Thrombocytopenia, Plasma Cell Disorders, and Waldenstrom's Macroglobulinemia.

In certain embodiments, the cells are used in autologous/heterologous tissue regeneration/replacement therapy, including treatment of corneal epithelial defects, cartilage repair, facial dermabrasion, burn and wound dressing for traumatic injuries of skin, mucosal membranes, tympanic membranes, intestinal linings, and neurological structures. For example, augmentation of myocardial performance can be achieved by the transplantation of cells into damaged myocardium (cellular cardiomyoplasty (CCM)), to enhance myocardial performance and treat end-stage cardiac disease. The cells may also be used for repair of a number of CNS disorders, for example, as described by Cao et al., 2002, "Stem cell repair of central nervous system injury," J Neuroscience Res 68: 501-510. The cells may also be used in reconstructive treatment of damaged tissue by surgical implantation of cell sheets, disaggregated cells, and cells embedded in carriers for regeneration of tissues for which differentiated cells have been produced. The cells may also be used in tissue engineered constructs. Such constructs comprise a biocompatible polymer formed into a scaffold suitable for cell growth. The scaffold can be shaped into a heat valve, vessel (tubular), planar construct or any other suitable shape. Such constructs are well known, such as those described in WO02/035992, and in U.S. Pat. Nos. 6,479,064, 6,461,628.

It will be appreciated that, for clarity purposes, the above description has described embodiments of the invention with reference to different functional units and/or modules of the cell collection device. However, it will be apparent that any suitable distribution of functionality between different functional units, modules or domains may be used without detracting from the invention. For example, functionality illustrated to be performed by separate modules may be performed by the same module. Hence, references to specific functional units are only to be seen as references to suitable means for providing the described functionality, rather than indicative of a strict logical or physical structure or organization.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosure may be described or claimed in the singular, the plural is contemplated to be within the scope thereof unless limitation to the singular is explicitly stated. For example, "a" device includes one or more devices. The presence of broadening words and phrases such as "one or more," "at least," "but not limited to", or other like phrases in some instances shall not be read to mean that the narrower case is intended or required in instances where such broadening phrases may be absent.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

EXAMPLES

The following examples are intended to further describe and illustrate various aspects of the invention, but not to limit, the scope of the invention in any manner, shape, or form, either explicitly or implicitly.

Example 1

Isolation of Cells from Freshly Harvested Umbilical Cord Blood

Freshly harvested umbilical cord blood was processed for mononuclear cell or CD34$^+$ cell isolation. Prior to freezing and liquid nitrogen storage for future applications, the endothelial progenitor cells were isolated from within the mononuclear and CD34+ population for separate cell expansion, freezing, storage, and reprogramming purposes. The total cord blood mononuclear cells, or magnetic bead isolated CD34+ hematopoietic stem and progenitor cells, were plated in a tissue culture dish coated with vitronectin, gelatin or collagen I. Following approximately 5-10 minutes incubation to allow cell adhesion, the hematopoietic cell fraction (which comprises the non-adherent cell fraction of the cord blood) was washed away with three washes of saline solution or similar medium. The hematopoietic cell fraction was processed via centrifugation at 350 RCF to obtain a pellet for resuspension in an appropriate freezing media for subsequent freezing and storage.

Figure 1:
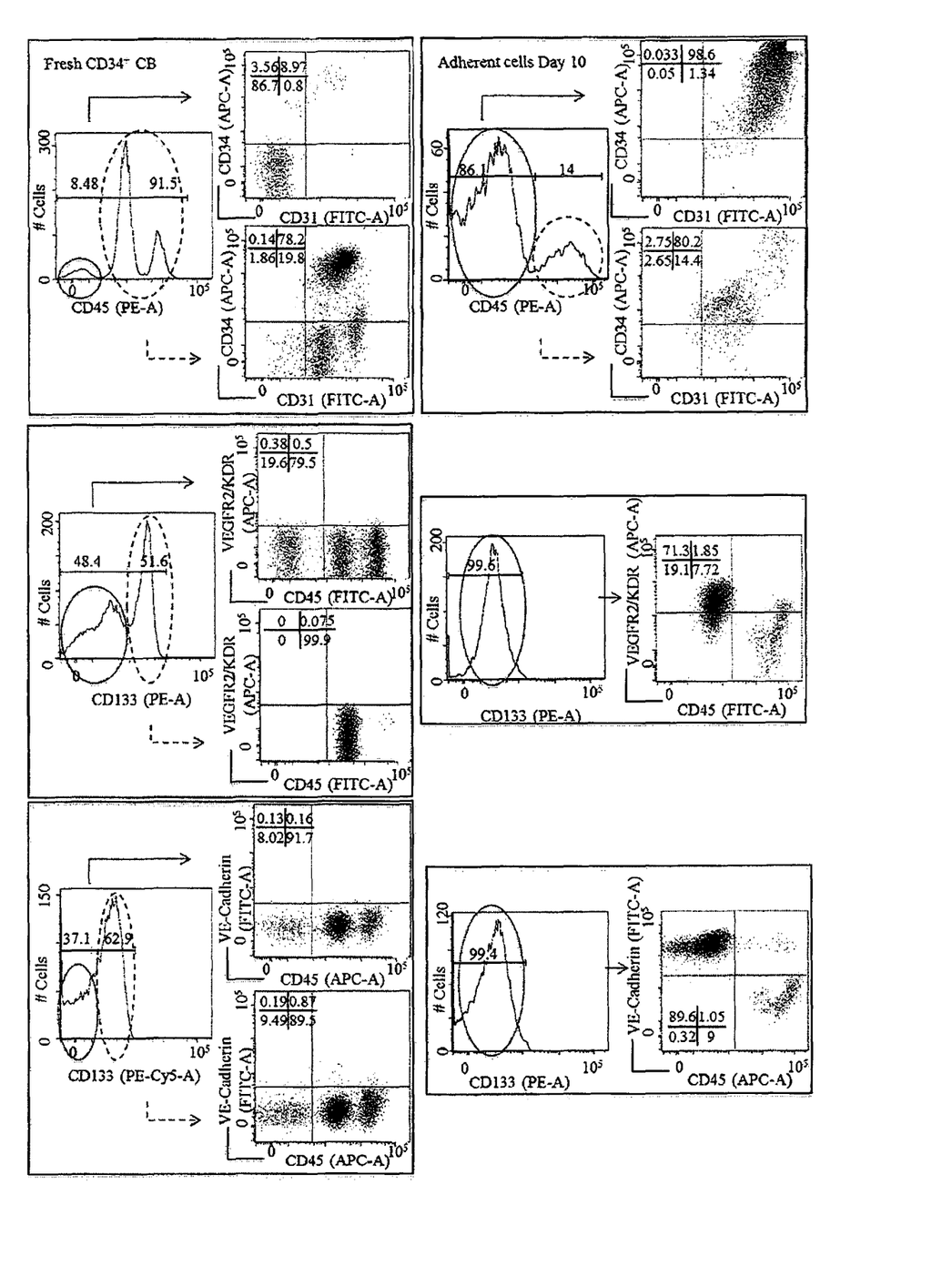
FIG. 1 illustrates cell surface marker expression of fresh $CD34^+$ cord blood cells and adherent cells (at day 10) measured by FACS analysis.

The remaining adherent endothelial cell progenitors were then cultured at 37° C. in commercially available endothelial cell medium until endothelial cell colonies formed or until plate confluency was reached following the initial plated cell expansion. The endothelial cell fraction was then frozen and stored in liquid nitrogen for future reprogramming uses. As shown in FIG. 1, the fresh cord blood cells contain both the endothelial cell fraction (CD45$^-$CD34$^+$CD31$^+$) and the hematopoietic fraction (CD45$^+$). Following total cell culturing for 10 days the endothelial cell fraction became the majority with an adherent CD34$^+$CD31$^+$ phenotype. Fresh cord blood cells also contain CD133$^+$ and negative cells with a low number of cells expressing the endothelial cell markers VE-cadherin and VEGFR2. Following 10 days of endothelial cell culture, the percentage of endothelia cells expressing VE-cadherin and VEGFR2 increases significantly.

Upon thawing of the endothelial cell fraction and plating, cells were cultured in endothelial cell media on a gelatin or collagen I coated tissue culture plate until 70% plate confluency. The cells were then transduced with lentiviral vectors of the reprogramming factors OCT4, SOX2, KLF4, C-MYC, and LIN28. The cells were reprogrammed to a pluripotent stem cell state, as validated by in vivo teratoma formation assays. The cells were transplanted into immune compromised mice, and the presence of all three germ layers was identified. Q-PCR for markers of pluripotency were also performed to confirm the pluripotent stem cell state of the reprogrammed endothelial cells isolated from cord blood. Pluripotent stem cells could then be differentiated into neuronal and hematopoietic cell lineages using the appropriate differentiation systems.

Example 2

Isolation of Cells from Frozen Umbilical Cord Blood

A frozen sample of mononuclear or CD34$^+$ cells isolated from cord blood was thawed and plated in a tissue culture dish coated with gelatin or collagen I. Following approximately 5-10 minutes incubation to allow cell adhesion, the hematopoietic cell fraction (which comprises the non-adherent cell fraction of the cord blood) was washed away with three washes of saline solution or similar medium. The hematopoietic cell fraction was processed via centrifugation at 350 RCF to obtain a pellet for resuspension in an appropriate freezing media for subsequent freezing and storage. The remaining adherent endothelial cell progenitors were then cultured at 37° C. in commercially available endothelial cell medium until endothelial cell colonies formed or until plate confluency was reached following the initial plated cell expansion. The endothelial cell fraction was then frozen and stored in liquid nitrogen for future reprogramming uses.

Example 3

A Device for Harvesting and Separation of Cells from Cord Blood

The invention also relates to a device for the efficient harvesting and separation of the cellular components of the cord blood material employing the principal workings of the method outlined above. One such embodiment comprises a sterile dual-vessel closed collection system, where one of the vessels is pre-coated for endothelial cell attachment. When the cord blood sample is ready for processing, either having been freshly harvested in a separate collection vessel, or having been processed for progenitor cell enrichment and placed in separate temporary storage vessel, or having been recently thawed in a storage vessel, the umbilical cord blood or enriched cells are transferred to the vessel with the endothelial cell adherence coating (vessel 1). The transfer of the cord blood material to vessel 1 can be performed by directly connecting vessel 1 to the collection/storage vessel containing blood or cells via a needle and catheter tubing from the vessel and into the coated vessel 1. Following transfer to vessel 1, cells are incubated for the appropriate time and at the appropriate temperature depending on the adherence factors used in the coating on a flat horizontal surface. Following the cell-adherence incubation step, the non-adherent fraction of cells in suspension is transferred to the hematopoietic cell collection vessel (vessel 2) which is connected to the coated bag via a sterile tubing. Wash medium stored in a separate sealed storage chamber attached to the vessel 1 can then be transferred into vessel 1, in three separate wash steps (25-100 mL each), using a stopcock valve or equivalent structure located on the tubing between the medium chamber and vessel 1. The wash media with suspension of hematopoietic cells is then transferred to the hematopoietic collection vessel (vessel 2) via a closed tubing also with a stopcock valve or other equivalent system. After the transfer, the adherent fraction in vessel 1 is re-submerged in media and an auxiliary chamber with cryoprotectant is opened to release an appropriate volume of cryoprotectant, and the adherent cells are directly frozen. Vessel 2 also has an auxiliary cryoprotectant buffer chamber, thus hematopoietic suspension can be frozen directly.

The pre-coated vessel 1 with attached needle and catheter tubing can be used to harvest cord blood directly from the cord. This allows the separation to proceed directly following the harvest. The separation of hematopoietic cells and endothelial cells occurs as detailed above. This system allows for a quick and simple processing of cord blood cell fractions in a closed system that can be performed with sterility at the bedside.

Throughout this application, various website data content, publications, patent applications and patents are referenced. (Websites are referenced by their Uniform Resource Locator, or URL, addresses on the World Wide Web.) The disclosure of each of these references is hereby incorporated by reference herein in its entirety.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

We claim:

1. A method for cell separation, comprising:
plating a freshly harvested umbilical cord blood sample that has not been enriched, stored, thawed, or washed on a surface at a surface density of approximately 100 million cells per 100 cm$^2$, the surface coated in a component configured to selectively bind with endothelial cells within the whole umbilical cord blood sample;
allowing adhesion of cells in said umbilical cord blood sample to said surface for about 5 minutes to about 60 minutes, to generate an adherent fraction and a non-adherent fraction of said whole umbilical cord blood sample;
separating said non-adherent fraction from said adherent fraction, wherein said non-adherent fraction comprises a hematogenic progenitor cell or a hematopoietic stem cell;
wherein said adherent fraction comprises at least one of an endothelial cell and an endothelial progenitor cell; and
processing and storing the non-adherent fraction.

2. The method of claim 1, wherein separating said non-adherent fraction from said adherent fraction does not cause detachment of the majority of the cells in said adherent fraction from the surface.

3. The method of claim 1, wherein about 10%, about 20%, about 30%, about 40%, about 50%, about 60%, about 70%, about 80%, or about 90% of cells in said adherent fraction remain attached to the surface following separating said non-adherent fraction from said adherent fraction.

4. The method of claim 1, wherein said umbilical cord blood sample is from a human.

5. The method of claim 1, wherein said umbilical cord blood sample is frozen and thawed before the plating step.

6. The method of claim 1, wherein the said umbilical cord blood sample is plated at a temperature between about 0° C. and about 37° C.

7. The method of claim 1, wherein the surface is coated with an extracellular matrix component.

8. The method of claim 7, wherein the extracellular matrix component is collagen I, gelatin, or a combination thereof.

9. The method of claim 1, wherein the cell viability, primitivity, proliferation ability, differentiation ability, and/or repopulating ability of the hematogenic progenitor cell or hematopoietic stem cell is maintained.

10. The method of claim 1, wherein the cell viability and/or primitivity of cells in the adherent fraction is maintained.

11. The method of claim 1, further comprising isolating an adherent cell from the adherent fraction and reprogramming the isolated adherent cell to a stem cell or progenitor cell.

12. The method of claim 1, further comprising expanding the hematogenic progenitor cell or hematopoietic stem cell.

13. The method of claim 12, further comprising:
(1) isolating a more primitive cell from the expanded hematogenic progenitor cell or hematopoietic stem cell population, or
(2) reprogramming said hematogenic progenitor cell or hematopoietic stem cell to a more primitive cell.

14. The method of claim 1, further comprising isolating an adherent cell from the adherent fraction, and:
(a) reprogramming the isolated adherent cell to a stem cell or progenitor cell, and differentiating said stem cell or progenitor cell to a somatic cell; or
(b) reprogramming the isolated adherent cell to a somatic cell directly.

15. The method of claim 1, wherein a device is used for cell separation from the umbilical cord blood sample, the device comprising a first vessel, a second vessel, and a sterile tubing with stopcock flow regulation for the transfer of cells in suspension between the vessels, and
wherein one of the vessels is pre-coated for cell attachment of cells in the adherent fraction, and the other vessel is a collection vessel for cells in the non-adherent fraction.

16. The method of claim 15, wherein the device is prefilled with a hypoxic, normoxic, or hyperoxic gas.

17. The method of claim 1, wherein said adherent fraction comprises a mesenchymal stem cell.

18. The method of claim 17, further comprising isolating said endothelial cell, endothelial progenitor cell, and/or mesenchymal stem cell from said adherent fraction.

19. The method of claim 1, further comprising isolating said hematogenic progenitor cell or hematopoietic stem cell from said non-adherent fraction.

20. The method of claim 1, further comprising using the non-adherent fraction for treatment of a hematologic disorder.

* * * * *